United States Patent [19]

Besançon et al.

[11] Patent Number: 4,762,852

[45] Date of Patent: Aug. 9, 1988

[54] BENZODIOXEPANNE, PROCESS FOR THE SYNTHESIS THEREOF AND USE THEREOF

[75] Inventors: Denis Besançon, Paris; Jacqueline Franceschini, l'Hay-les-Roses, both of France

[73] Assignee: Societe d'Etudes Scientifiques et Industrielles de l'Ile de France, Paris, France

[21] Appl. No.: 895,881

[22] Filed: Aug. 12, 1986

[30] Foreign Application Priority Data

Aug. 12, 1985 [FR] France ................. 85 12270

[51] Int. Cl.$^4$ .................. A61K 31/40; C07D 405/12; C07D 31/335
[52] U.S. Cl. ................. 514/422; 548/526; 549/350
[58] Field of Search .......... 548/526; 514/422

[56] References Cited

U.S. PATENT DOCUMENTS

| | | | |
|---|---|---|---|
| 3,864,486 | 2/1975 | Blum | 514/221 |
| 4,186,135 | 1/1980 | Thominet et al. | 548/526 |
| 4,248,885 | 2/1981 | Thominet et al. | 514/422 |
| 4,379,161 | 4/1983 | Thominet et al. | 548/570 X |

FOREIGN PATENT DOCUMENTS 2901170 7/1979 Fed. Rep. of Germany ...... 548/567

OTHER PUBLICATIONS

The Merck Index, 9th ed. (1976), p. 1165, entry 8786.
Lipton, et al. "Psychopharmacology: A Generation of Progress", pp. 1067–1068 (1978).
Puech, et al., Europ. J. Pharmacol., 50, pp. 291–300 (1978).
Janssen, et al., Arzn. Forsch., 10, pp. 1003–1005 (1960).
Janssen, Arzn. Forsch, 11, pp. 932–938 (1961).
Cerletti, et al., Arz. Forsch, 12, pp. 964–968 (1962).

Primary Examiner—Donald G. Daus
Assistant Examiner—William A. Teoli, Jr.
Attorney, Agent, or Firm—Fitzpatrick, Cella, Harper & Scinto

[57] ABSTRACT

The compound of N-(1-cyclohexenylmethyl)2-pyrrolidinymethyl 8-ethylsulphonyl-1,5-benzodioxepanne-6-carboxamide is useful to treat psychoses.

4 Claims, No Drawings

BENZODIOXEPANNE, PROCESS FOR THE SYNTHESIS THEREOF AND USE THEREOF

The present invention concerns N-(1-cyclohexenylmethyl 2-pyrrolidinylmethyl)-8-ethylsulphonyl-1,5-benzodioxepanne -carboxamide, a novel compound corresponding to the following formula:

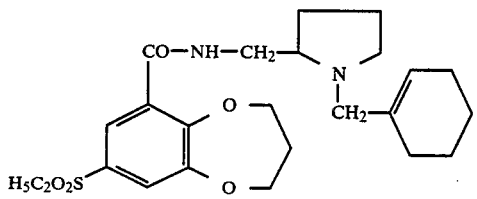

and the pharmacologically acceptable salts thereof.

The compound according to the invention has pharmacological characteristics which justify the use thereof in therapeutics as a powerful, rapid neuroleptic agent. It may be prepared by reacting 8-ethylsulphonyl 1,5-benzodioxepanne 6-carboxylic acid with thionyl chloride, resulting in the corresponding acid chloride, then reacting the 8-ethylsulphonyl-1,5-benzodioxepanne 6-carbonyl chloride with 1-(1-cyclohexenylmethyl) 2-aminomethyl pyrrolidine. The precursor 8-ethylsulphonyl-1,5-benzodioxepanne 6-carboxylic acid is itself prepared by first treating 1,5-benzodioxepanne 6-carboxylic acid with sulphuric chlorohydrin, then converting the resulting 8-chlorosulphonyl-1,5-benzodioxepanne-6-carboxylic acid obtained, by a reduction reaction and then an ethylation reaction to give the desired acid. The following example illustrates synthesis of subject compound of the invention, in accordance with the following reaction diagram:

I - 8-Chlorosulphonyl-1,5-benzodioxepanne-6-carboxylic acid

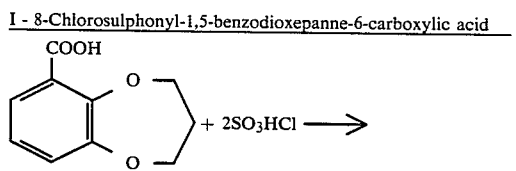

II - 8-Ethylsulphonyl-1,5-benzodioxepanne-6-carboxylic acid

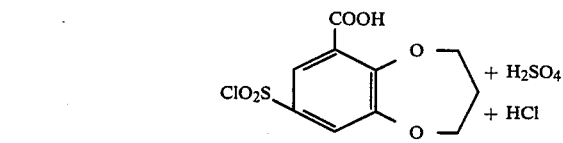

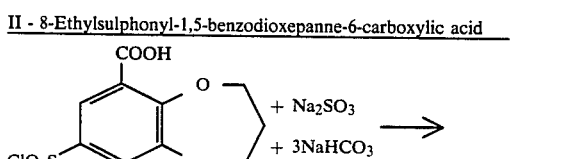

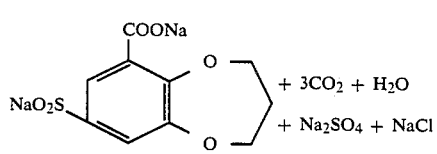

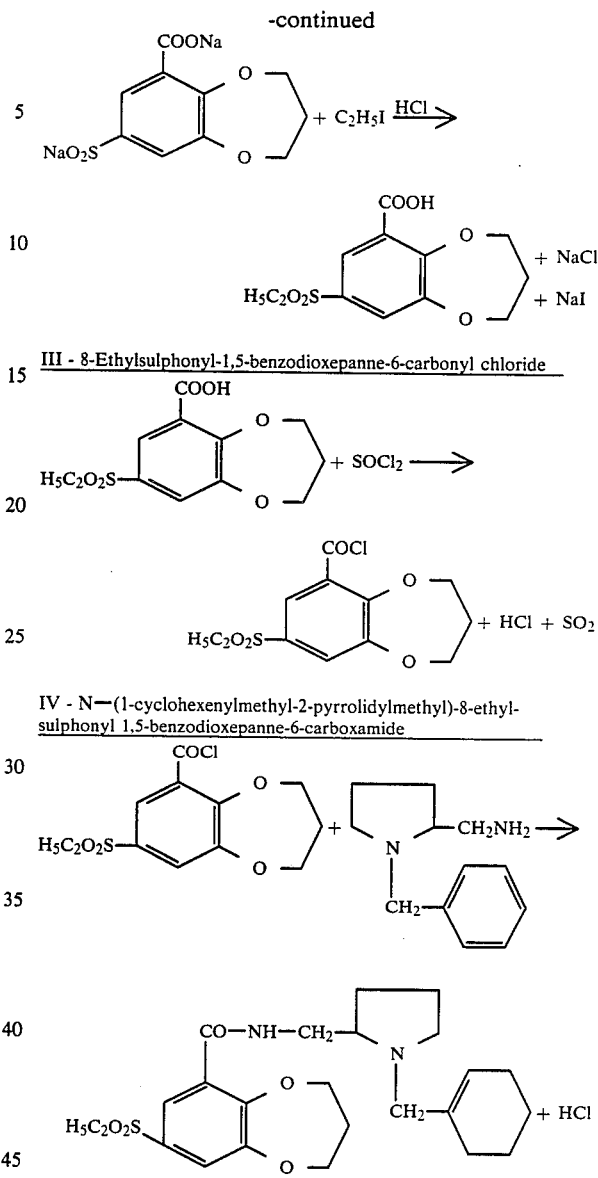

III - 8-Ethylsulphonyl-1,5-benzodioxepanne-6-carbonyl chloride

IV - N—(1-cyclohexenylmethyl-2-pyrrolidylmethyl)-8-ethylsulphonyl 1,5-benzodioxepanne-6-carboxamide In the following Example certain preferred embodiments are illustrated.

EXAMPLE 1

Step 1: 8-CHLOROSULPHONYL-1,5-BENZODIOXEPANNE 6-CARBOXYLIC ACID

Using a three liter balloon flask provided with a sealed agitator, a reflux condenser and a thermometer, 1092 ml of sulphuric chlorohydrin (2 liters/mole) was introduced, and then, in portions, 106 g of 1,5-benzodioxepanne 6-carboxylic acid (0.546 mole). The temperature was maintained at between 5 and 10° by external cooling. Each portion of acid dissolved instantly. When the introduction of the materials was concluded, the temperature was allowed to rise and agitation was continued for 5 hours. The reaction mixture was then left overnight at ambient temperature. 7.5 kg of ice was introduced into a six liter balloon flask provided with an agitator, a thermometer and a dropping funnel and the sulphochloride solution was poured in dropwise. External cooling was effected by means of dry ice so as to maintain the temperature at between 0° and 5°. The introduction operation took 35 minutes. The sulphochloride crystallized immediately. The resulting product was drained off, washed with water until the Cl⁻ ions were removed, and dried in the air.

Weight obtained = 146 g
Yield = 91%
MP = 114°–115°.

Step 2:
8-ETHYLSULPHONYL-1,5-BENZODIOXEPANNE-6-CARBOXYLIC ACID

A—Reduction of chlorosulphonyl group to sodium sulfonyl group

Using a 10 liter balloon flask provided with a sealed agitator, a double-casing reflux condenser and a thermometer, 1086 cc of water, 236 g of sodium sulphite (1.25 mole +50% excess) and 315 g of sodium bicarbonate (1.25 mole×3) were introduced, and heating at 65° to 70° was effected. 365 g of 8-chlorosulphonyl 1,5 benzodioxepanne 6-carboxylic acid (1.25 mole) from Step 1 was then added in portions. A substantial amount of carbon dioxide gas was given off. The introduction operation was conducted for about 2 hours. Heating was then continued at 70° to 80° until the gas ceased being evolved. A weight loss of 152 g was then observed, for a theoretical value of 165 g.

B—Ethylation of sulphonyl group to ethyl sulphonyl group

After cooling, 1296 cc of ethanol, 585 g of ethyl iodide (1.25 mole×3) and 80 cc of 30% soda lye were added to the product of Step 2(A) so that the medium was alkaline to phenolphthalein. The mixture was heated under reflux for 16 hours, with the addition of soda lye as soon as the medium was no longer alkaline, and with compensation in respect of the losses of ethyl iodide, if such occurred. At the end of the reaction, heating under reflux in an alkaline medium was carried out for a period of 4 hours. The total duration of the reaction was 20 hours. The major part of the alcohol was, distilled and the residue was dissolved in 3 liters of water. The resulting solution was filtered with carbon black and then acidified with 400 cc of concentrated hydrochloric acid. The acid which precipitated was drained off washed with water until the Cl⁻ ions were removed, and dried at 50° C.

Weight obtained = 311 g
Yield = 84%
MP = 143°.

Step 3:
8-ETHYLSULPHONYL-1,5-BENZODIOXEPANNE-6-CARBONYL CHLORIDE

Using a 500 cc balloon flask provided with a reflux condenser, 200 g of thionyl chloride (0.42 mole×4) was introduced, followed then by approximately half the total amount required of 8-ethylsulphonyl-1,5-benzodioxepanne 6-carboxylic acid (0.42 mole, or 120 g). Heating was effected on a water bath at 40° until the acid was largely dissolved. The second half was then added and heating was gradually effected to 50° C., and then under reflux, until total dissolution occurred. The excess of thionyl chloride was then distilled under vacuum until a constant weiqht was attained. The remaining acid chloride crystallized.

Weight obtained = 123 g
Yield = 96%
MP = 125°.

Step 4:
N-(1-CYCLOHEXENYLMETHYL-2-PYRROLIDYLMETHYL) 8-ETHYLSULPHONYL-1,5-BENZODIOXEPANNE-6-CARBOXAMIDE Using a two liter balloon flask provided with an agitator, a thermometer and a dropping funnel, 78 g of 1-(1-cyclohexenylmethyl) 2-aminomethyl pyrrolidine (0.404 mole) and 600 cc of chloroform were introduced. To the resulting solution there was gradually added 123 g of 8-ethylsulphonyl 1,5-benzodioxepanne 6-carbonyl chloride (0.404 mole) from Step 3 in finely powdered form. The chloride compound dissolved as it was added. At the end of the introduction operation, the hydrochloride form crystallized. Agitation was maintained for a further hour at 10° C. and then the crystals were drained off, washed with methylethylketone and finally with ether, and then dried in the air.

Weight obtained = 144 g
Yield = 71.5%.

The 144 g of hydrochloride and 48 g from earlier syntheses, namely 192 g in all, were dissolved in 800 cc of water. The solution obtained was filtered with carbon black and then made alkaline by means of 50 cc of soda lye. The base which precipitated in pasty form was extracted with methylene chloride. The chloromethylenic solution was dried over potassium carbonate and then methylene chloride was distilled, terminating under vacuum, until a constant weight was attained. The residue, 173 g, was redissolved in 520 cc of 95% alcohol. Crystallization was initiated by seeding and, thereafter, developed slowly. After about 3 hours, the crystals obtained were drained off, washed with 95% alcohol and finally with ether, and then dried in the air.

Weight obtained = 119 g
MP = 103°
Yield with respect to the hydrochloride = 67%.

The product formed, N-(1-cyclohexenylmethyl-2 pyrrolidylmethyl)-8-ethylsulphonyl-1,5-benzodioxepanne 6-carboxamide, had the following characteristics:

(i) White crystals.
(ii) Soluble in dilute acids.
(iii) Highly soluble in hot methanol (2 volumes); very weakly soluble when cold.
(iv) Highly soluble in hot ethyl acetate (2 volumes); soluble when cold in 30 volumes.
(v) MP (Buchi) = 102°–104°.

The compound of the invention was subjected to pharmacological tests which have the following results:

(1) The compound bound very strongly in-vitro to dopaminergic $D_2$ receptors. In fact, in regard to that class of receptors, using the ligand [3] H-spiperone which marks them, we found a $IC_{50}$ of $3.16 \times 10^{-9}M$ whereas binding to the $D_1$ receptor was weak ($IC_{50} = 2.49$ or $6.31 \times 10^{-5}M$) against $^3$H-piflutixol. That strong $D_2$ binding suggested a powerful action on such receptors, diffusion of the product at the level thereof also appeared to be possible under good conditions with a partition coefficient of 3.3.

(2) The compound of the invention was a powerful anti-dopaminergic agent at the level of the central nervous system. Indeed, in the test in respect of stereotypies caused in rats by apomorphine, a dopaminergic agonistic agent, the compound antagonized that behavioral response at very low levels. Thus, when stereotypies were caused by 0.5 mg/kg of subcutaneous apomorphine, the inhibitor-50 dose of the compound was 0.52 mg/kg intraperitoneally. This test was conducted in accordance with the procedure in Europ. J. Pharmacol., 50, pp. 291-300 (1978). It was even more active when injected subcutaneously: $ID_{50}=0.039$ mg/kg. When the dose of apomorphine was greater, 1.25 mg/kg intravenous (test procedure as described in Arzn. Forsch. 10, pp. 1003-1005, (1960), the compound which was injected subcutaneously still had a very powerful antagonism, the $ID_{50}$ being 0.092 or 0.082 mg/kg. Likewise, the compound powerfully antagonized stereotypies which are caused in a rat by amphetamine, another dopaminergic agonistic agent, in an intravenous dosage of 10 mg/kg when conducted according to Arz. Forsch. 11, pp. 932-938 (1961). In that case, the inhibitor dose 50 of the compound was also low, 0.062 mg/kg subcutaneously. Under other experimental conditions, amphetamine being injected intraperitoneally, the $ID_{50}$ of the compound was 0.4 mg/kg. From those results, it was demonstrated that the compound was highly effective in resisting the central effects of the dopaminergic agonistic agents, apomorphine and amphetamine, and that consequently it possessed to a very high degree, a property which is characteristic of neuroleptic agents. In that respect, it is markedly superior to a chemically related derivative N-(1-ethyl-2-pyrrolidinylmethyl) 8-ethylsulphonyl-1,5-benzodioxepanne-6-carboxamide (reference compound), whose inhibitor doses 50 are much higher, demonstrating a much lower level of power in respect of neuroleptic effect. Thus, with the reference compound, the $ID_{50}$ in a rat was 156 mg/kg subcutaneously, against 1.25 mg/kg of intravenous apomorphine and 36.4 mg/kg intraperitoneally against 0.5 mg/kg of subcutaneous apomorphine. Likewise, this reference compound antagonized amphetamine only at an elevated $ID_{50}=39.4$ mg/kg subcutaneous. The reference compound is disclosed in U.S. Pat. Nos. 4,186,135 (Example 43) and 4,248,885.

(3) The neuroleptic property of the compound of the invention was further demonstrated by the fact that it had a cataleptigenic effect, another characteristic of neuroleptic agents. The cataleptigenic dose 50, as determined in accordance with Arz. Forsch. 12, pp. 964-968 (1962), was 5.3 mg/kg subcutaneously in a rat. Another test gave a value which was slightly higher, 8.5 mg/kg subcutaneous, also in a rat. In contrast, the reference compound was much less cataleptigenic, the $ED_{50}$ being 59.5 mg/kg subcutaneously, confirming the lower activity of that compound in comparison with that of the inventive compound.

(4) The compound according to the invention had the remarkable property of rapidly performing its neuroleptic effect and, on the other hand, having a prolonged effect. Thus, in tests in respect of stetectypies in relation to amphetamine in a rat, the antagonistic action with the $ID_{50}$ reported above (0.4 mg/kg subcutaneous) was already found to occur at the 12th minute after the subcutaneous injection of the compound.

In another test, the inhibitor doses 50 of the compound were evaluated according to Europ. J. Pharm. 50, pp. 291-300 (1978), the compound being administered at different times (15, 30, 60, 120 and 360 minutes) prior to administration of the agonistic agent, in this case apomorphine, in a dose of 0.5 mg/kg subcutaneous.

It is thus possible to judge the power of the antagonism produced by the compound at those different times and also to evaluate the duration of the effect of the compound. The $ID_{50}$ when evaluated under those conditions was 0.066 mg/kg subcutaneous, the test being carried out 15 minutes after the injection. Then, for periods of 30 to 360 minutes, the ID 50 was between 0.035 and 0.049 mg/kg subcutaneous, which indicated the permanence of a marked neuroleptic action. The kinetics of the action of the compound of the invention, indicating the rapid establishment of the neuroleptic effect and the long duration thereof, were also demonstrated by observation of the cataleptigenic effect. Catalepsy appeared in fact, 11 minutes after subcutaneous injection of the compound and lasted for more than 5 hours and up to 12 hours in a rat, depending on the method of observation of the phenomenon.

(5) The compound of the invention reduced spontaneous motility of a mouse. When administered intraperitoneally, the $ID_{50}$ then being 0.58 to 0.93 mg/kg depending on the test procedure, or orally, the $ID_{50}$ then being 13.2 to 16.4 mg/kg. When the ID 50 was 0.58 mg/kg the test procedure used was as in Pharm. Exp. Ther. 101, pp. 156-162 (1951). When the test yielded an $ID_{50}$ of 0.93 mg/kg., the test procedure used was the Activograph Method in which mouse movements were detected as pressure variations on the floor of the cage.

The kinetics of the inhibitor effect of the compound were studied in mice by evaluation of the inhibitor doses 50 at different distances from intraperitoneal injection of the compound. The procedure used was the photoelectric method described in J. Pharm. Exp. Ther. 101, pp. 156-162 (1951). After 5 minutes, the $ID_{50}$ of 0.69 mg/kg demonstrated that the inhibitor effect was already powerful. Then, the variation in the $ID_{50}$ between 0.55 and 0.9 indicated persistence of the effect up to 5 hours. The effect then became less clear, but could still be observed more than 5 hours after administration, which is in accordance with the duration attributed to the cataleptigenic effect.

(6) The compound of the invention had a remarkable and unexpected property; namely, that at very low dosage levels where its neuroleptic effect is not apparent, it has a certain activating effect which is shown by an increase in motor activity as measured by a photoelectric process. Such activation occurs significantly at doses of between 0.0001 and 0.5 mg/kg subcutaneous. On the other hand, at the higher neuroleptic doses which reduce motor function, the animals treated by the compound retain a certain degree of vigilance; in particular, they keep their eyes open, which is unusual with powerful neuroleptics. The compound of the invention has the pharmacological characteristics of a powerful neuroleptic, acting rapidly and in a long-term fashion, and, consequently, can be applied in states of agitation of acute and chronic psychoses. For this and other purposes the daily therapeutic dosage can be from about 5 to 50 mg/day in one or more doses, depending upon the severity of the psychoses. The compound of the invention can be administered in any number of conventional forms such as capsules, tablets, pills, in granulated form or as an injectable solution. Many methods for compounding these preparations are well-known to the art. Substances (or carriers) which are inert relative to the compounds of the invention can be used in these preparations, such as lactose, magnesium stearate, starch, talc, cellulose, levilite, alkali metal lauryl-sulphates, saccharose and other vehicles and carriers commonly employed in pharamaceutical preparations. The examples which follow illustrate several possible pharmaceutical preparations.

EXAMPLE 2 tablets

| | |
|---|---|
| N—(1-cyclohexenylmethyl)2-pyrrolidinylmethyl 8-ethylsulphonyl-1,5-benzodioxepanne-6-carboxamide | 5 mg |
| dried starch | 20 mg |
| lactose | 100 mg |
| methylcellulose 1500 cps | 1.5 mg |
| levilite | 10 mg |
| magnesium stearate | 4 mg |
| for 1 tablet. | |

EXAMPLE 3 capsules

| | |
|---|---|
| N—(1-cyclohexenylmethyl)2-pyrolidenylmethyl 8-ethylsulphonyl-1,5-benzodioxepanne-6-carboxamide | 50 mg |
| microcrystalline cellulose | 50 mg |
| methylcellulose 1500 cps | 1 mg |
| magnesium stearate | 5 mg |
| talc | 2 mg |
| for 1 capsule. | |

EXAMPLE 4 injectable solution

| | |
|---|---|
| N—(1-cyclohexenylmethyl)-2-pyrrolidinylmethyl 8-ethylsulphonyl-1,5-benzodioxepanne-6-carboxamide | 40 mg |
| 1N hydrochloric acid | 0.1 ml |
| sodium chloride | 14 mg |
| for 2 ml. | |

EXAMPLE 5 injectable solution

| | |
|---|---|
| N—(1-cyclohexenylmethyl)2-pyrrolidinylmethyl 8-ethylsulphonyl-1,5-benzodioxepanne-6-carboxamide | 20 mg |
| 1N hydrochloric acid | 0.250 ml |
| sodium chloride | 8 mg |
| for 2 ml. | |

To prepare the tablets, the compound is mixed with the starch and lactose by the method of successive dilutions; the mixture is granulated with methylcellulose. The levilite, magnesium stearate and talc are added to the granules before proceeding with compression.

It is possible to replace the methylcellulose with any other appropriate granulating agent, such as ethylcellulose, polyvinylpyrrrolidone or starch paste. The magnesium stearate may be replaced by stearic acid.

When preparing injectable solutions, it is possible to dissolve the compound of the invention in the following acids: hydrochloric or levulinic acid, gluconic acid, or glucoheptonic acid. The solution is prepared under sterile conditions and made isotonic with an alkali metal chloride such as sodium chloride, then preservatives are added. It is also possible to prepare the same solution without adding any preservatives: the ampoule is then filled under nitrogen and sterilized or ½ hour at 100° C. The pharmacologically acceptable salts of the compound of the invention include the non-toxic acid addition salts formed by reacting the benzamide of the invention with the desired acid. The acid may be an inorganic acid, such as sulfuric, sulfamic, nitric, hydrobromic, hydrochloric, phosphoric and the like or an organic acid, such as citric, tartaric, lactic, acetic, succinic, fumaric, maleic, benzoic and the like.

The pharmacologically acceptable salts of the compound of the invention also include the non-toxic quaternary ammonium salts produced by reacting the benzamide with an aliphatic or aromatic alkylating agent, such as methyl chloride, methyl bromide, dimethyl sulfate, methyl p-toluene sulfonate and the like. In addition, the benzamide compound includes the N-oxides formed by utilizing the conventional oxidizing agents; see, for example, U.S. Pat. No. 3,839,330, issued Oct. 1, 1974.

This invention is not to be limited except as set forth in the following claims:

What is claimed is:

1. N-(1-cyclohexenylmethyl-2-pyrrolidinylmethyl)-8-ethylsulphonyl-1,5-benzodioxepanne-6-carboxamide and the pharmacologically acceptable salts thereof.

2. A pharmaceutical composition for the treatment of psychoses comprising an effective amount of the compound of claim 1 and a pharmacologically acceptable carrier.

3. A method for treating a patient exhibiting the symptoms of psychosis by administering to said patient a therapeutically effective amount of the compound of claim 1 sufficient to suppress said symptoms.

4. The method of claim 3 in which the therapeutic amount is from about 5 to 50 mg/day.

* * * * *